(12) United States Patent
Terrill

(10) Patent No.: US 12,109,122 B2
(45) Date of Patent: Oct. 8, 2024

(54) AUGMENTED GLENOID DESIGN

(71) Applicant: Howmedica Osteonics Corp., Mahwah, NJ (US)

(72) Inventor: Lance N. Terrill, League City, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 74 days.

(21) Appl. No.: 17/585,889

(22) Filed: Jan. 27, 2022

(65) Prior Publication Data

US 2022/0142787 A1 May 12, 2022

Related U.S. Application Data

(62) Division of application No. 16/925,809, filed on Jul. 10, 2020, now Pat. No. 11,285,009.

(60) Provisional application No. 62/873,266, filed on Jul. 12, 2019.

(51) Int. Cl.
*A61F 2/40* (2006.01)
*A61F 2/30* (2006.01)

(52) U.S. Cl.
CPC ........ *A61F 2/4081* (2013.01); *A61F 2/30771* (2013.01); *A61F 2002/30843* (2013.01); *A61F 2002/3092* (2013.01); *A61F 2002/4085* (2013.01)

(58) Field of Classification Search
CPC .. A61F 2/34; A61F 2/3872; A61F 2/40; A61F 2/4003; A61F 2/4014; A61F 2/4607; A61F 2/4609; A61F 2/4637; A61F 2/4081; A61F 2/30771; A61F 2002/30843; A61F 2002/3092; A61F 2002/4085; A61F 2002/30878; A61F 2002/30891;

(Continued)

(56) References Cited

U.S. PATENT DOCUMENTS 3,559,514 A 2/1971 Brownfield
5,203,653 A 4/1993 Kudla
(Continued)

FOREIGN PATENT DOCUMENTS

WO 2011149590 A1 12/2011

OTHER PUBLICATIONS

Extended European Search Report issued in Appln. No. 22171189.8 mailed Jul. 28, 2022 (2 pages).

(Continued)

*Primary Examiner* — Ann Schillinger
(74) *Attorney, Agent, or Firm* — Lerner David LLP

(57) ABSTRACT

A glenoid implant may include an articulating surface, a bone contacting surface opposite the articulating surface, and at least one anchor. The bone contacting surface may include a first portion with a first convexity configured to contact a first portion of the glenoid and a second portion with a second convexity configured to contact a second portion of the glenoid. The first convexity may be different than the second convexity. The implant may include a bearing component defining the articulating surface and an augment component defining at least a portion of the bone contacting surface. Anchors or protrusions may extend from the bone contacting surface. The anchors may include a substantially planar surface.

19 Claims, 7 Drawing Sheets

(58) Field of Classification Search
CPC .. A61F 2002/30892; A61F 2002/30841; A61F 2002/30736; A61F 2/30734
See application file for complete search history.

(56) References Cited

U.S. PATENT DOCUMENTS

| | | | |
|---|---|---|---|
| 5,458,637 A * | 10/1995 | Hayes | A61F 2/30734 623/23.28 |
| 5,591,170 A | 1/1997 | Spievack et al. | |
| 5,702,447 A * | 12/1997 | Walch | A61F 2/4081 606/327 |
| 5,800,551 A | 9/1998 | Williamson et al. | |
| 5,919,195 A | 7/1999 | Wilson et al. | |
| 6,699,289 B2 | 3/2004 | Iannotti et al. | |
| 6,949,101 B2 | 9/2005 | McCleary et al. | |
| 7,217,271 B2 | 5/2007 | Wolford et al. | |
| 7,473,254 B2 | 1/2009 | White et al. | |
| 7,503,921 B2 | 3/2009 | Berthusen et al. | |
| 7,572,259 B2 | 8/2009 | Desarzens et al. | |
| 7,637,909 B2 | 12/2009 | Lechot et al. | |
| 7,749,227 B2 | 7/2010 | Lechot et al. | |
| 7,780,669 B2 | 8/2010 | Lechot et al. | |
| 7,785,329 B2 | 8/2010 | Lechot et al. | |
| 7,803,160 B2 | 9/2010 | Keller | |
| 7,819,875 B2 | 10/2010 | Chana | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 8,052,690 B2 | 11/2011 | Berthusen et al. | |
| 8,206,453 B2 * | 6/2012 | Cooney, III | A61F 2/4261 623/21.12 |
| 8,241,365 B2 * | 8/2012 | Williams, Jr. | A61F 2/4081 623/19.11 |
| 8,282,639 B2 | 10/2012 | Chana | |
| 8,287,600 B2 * | 10/2012 | Angibaud | A61F 2/389 623/20.15 |
| 8,475,460 B1 | 7/2013 | Roger et al. | |
| 8,480,674 B1 | 7/2013 | Roger et al. | |
| 8,480,750 B2 * | 7/2013 | Long | A61F 2/40 623/19.11 |
| 8,486,076 B2 | 7/2013 | Chavarria et al. | |
| 8,657,833 B2 | 2/2014 | Burgi et al. | |
| 8,657,834 B2 | 2/2014 | Burgi | |
| 8,721,727 B2 | 5/2014 | Ratron et al. | |
| 8,740,907 B2 | 6/2014 | Penenberg | |
| 8,771,275 B2 | 7/2014 | Xie et al. | |
| 8,864,834 B2 | 10/2014 | Boileau et al. | |
| 9,066,730 B2 | 6/2015 | McMinn et al. | |
| 9,066,731 B2 | 6/2015 | Moore | |
| 9,078,672 B1 | 7/2015 | Rosse | |
| 9,248,022 B2 * | 2/2016 | Lappin | A61F 2/4081 |
| 9,408,652 B2 | 8/2016 | Hassler et al. | |
| 9,414,927 B2 * | 8/2016 | Iannotti | A61F 2/4003 |
| 9,498,334 B2 * | 11/2016 | Lappin | A61F 2/30734 |
| 9,498,345 B2 * | 11/2016 | Burkhead, Jr. | A61F 2/4081 |
| 9,844,440 B2 * | 12/2017 | Kovacs | A61F 2/30734 |
| 10,028,838 B2 * | 7/2018 | Hodorek | A61B 17/1684 |
| 10,350,078 B2 | 7/2019 | Ek et al. | |
| 10,555,816 B1 | 2/2020 | Pappou | |
| 11,103,357 B2 * | 8/2021 | Gargac | A61F 2/4081 |
| 11,141,276 B2 * | 10/2021 | Kehres | A61F 2/30734 |
| 11,730,604 B2 * | 8/2023 | Frankle | A61F 2/30734 623/19.12 |
| 2003/0163135 A1 | 8/2003 | Hathaway | |
| 2003/0220646 A1 | 11/2003 | Thelen et al. | |
| 2004/0097947 A1 | 5/2004 | Wolford et al. | |
| 2004/0236339 A1 | 11/2004 | Pepper | |
| 2005/0159751 A1 | 7/2005 | Berthusen et al. | |
| 2006/0015110 A1 | 1/2006 | Pepper | |
| 2006/0058809 A1 | 3/2006 | Zink et al. | |
| 2006/0200248 A1 * | 9/2006 | Beguin | A61F 2/4081 623/19.11 |
| 2007/0038302 A1 | 2/2007 | Shultz et al. | |
| 2007/0038303 A1 | 2/2007 | Myerson et al. | |
| 2007/0093840 A1 | 4/2007 | Pacelli et al. | |
| 2007/0100458 A1 * | 5/2007 | Dalla Pria | A61F 2/4081 623/19.13 |
| 2007/0179624 A1 * | 8/2007 | Stone | A61F 2/4081 623/22.36 |
| 2008/0262624 A1 | 10/2008 | White et al. | |
| 2008/0294268 A1 * | 11/2008 | Baum | A61F 2/4081 623/18.11 |
| 2009/0270863 A1 | 10/2009 | Maisonneuve | |
| 2010/0161066 A1 * | 6/2010 | Iannotti | A61F 2/4081 606/301 |
| 2010/0228352 A1 | 9/2010 | Courtney, Jr. et al. | |
| 2010/0274359 A1 * | 10/2010 | Brunnarius | A61F 2/30734 623/19.13 |
| 2011/0004215 A1 | 1/2011 | Bradley et al. | |
| 2012/0109229 A1 | 5/2012 | Forsell | |
| 2012/0123419 A1 | 5/2012 | Purdy et al. | |
| 2012/0221111 A1 * | 8/2012 | Burkhead, Jr. | A61F 2/4081 623/19.11 |
| 2012/0239042 A1 | 9/2012 | Lappin et al. | |
| 2013/0144393 A1 | 6/2013 | Mutchler et al. | |
| 2013/0150972 A1 * | 6/2013 | Iannotti | A61F 2/4059 623/18.11 |
| 2013/0150973 A1 * | 6/2013 | Splieth | A61F 2/4081 623/19.11 |
| 2014/0025173 A1 * | 1/2014 | Cardon | A61F 2/4081 623/19.13 |
| 2014/0031945 A1 | 1/2014 | Baptista et al. | |
| 2014/0257495 A1 | 9/2014 | Goldberg | |
| 2014/0257499 A1 * | 9/2014 | Winslow | A61F 2/4081 623/19.13 |
| 2014/0277518 A1 * | 9/2014 | Iannotti | A61F 2/30 623/19.11 |
| 2015/0150688 A1 | 6/2015 | Vanasse et al. | |
| 2015/0374502 A1 | 12/2015 | Hodorek et al. | |
| 2016/0166392 A1 * | 6/2016 | Vanasse | A61F 2/4612 700/98 |
| 2016/0270922 A1 * | 9/2016 | Pressacco | A61F 2/30749 |
| 2016/0310285 A1 | 10/2016 | Kovacs et al. | |
| 2016/0367375 A1 * | 12/2016 | Boulris | A61B 17/1684 |
| 2018/0303619 A1 | 10/2018 | Kehres et al. | |
| 2018/0333268 A1 * | 11/2018 | Cardon | A61F 2/30734 |
| 2019/0159906 A1 * | 5/2019 | Knox | A61F 2/40 |
| 2020/0405491 A1 * | 12/2020 | Cleveland | A61F 2/30749 |

OTHER PUBLICATIONS

Knowles, Nikolas K., "Osteoarthritis Induced Glenoid Morphology and Bone Quality: An Evaluation of Augmented Glenoid Components", Apr. 15, 2015, Electronic Thesis and Dissertation Repository. 2752, 172 pages, <https://ir.lib.uwo.ca/etd/2752>.

Knowles, Nikolas K et al. "Augmented glenoid component designs for type B2 erosions: a computational comparison by volume of bone removal and quality of remaining bone." Journal of shoulder and elbow surgery vol. 24,8 (Jan. 31, 2015): 1218-26. doi:10.1016/j.jse.2014.12.018.

McGuire, DT, Vrettos, B, Roche, S, & Walters, J. (Jan. 2012). Bone loss in shoulder replacement surgery: a review of current management. SA Orthopaedic Journal, 11(3), 47-55. Retrieved Jul. 9, 2020, from <http://www.scielo.org.za/scielo.php?script=sci_arttext&pid=S1681-150X2012000300005&lng=en&tlng=en>.

Karelse, Anne, et al. "Rocking-horse phenomenon of the glenoid component: the importance of inclination." Journal of Shoulder and Elbow Surgery 24.7 (Mar. 11, 2015): 1142-1148.

Knowles, N. K., Ferreira, L. M., & Athwal, G. S. (Jan. 23, 2016). The arthritic glenoid: anatomy and arthroplasty designs. Current reviews in musculoskeletal medicine, 9(1), 23-29. <https://doi.org/10.1007/s12178-016-9314-2>.

Extended European Search Report including Written Opinion for Application No. EP20185044.3, dated Nov. 17, 2020, pp. 1-6.

* cited by examiner

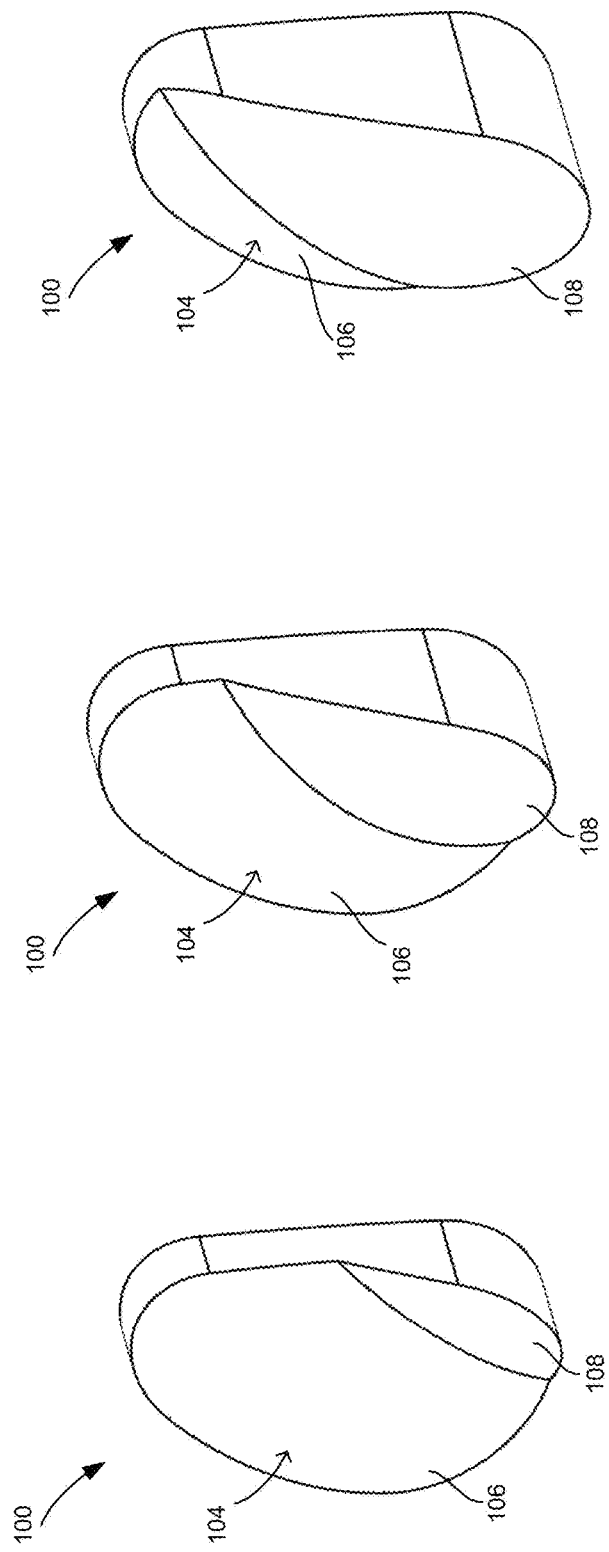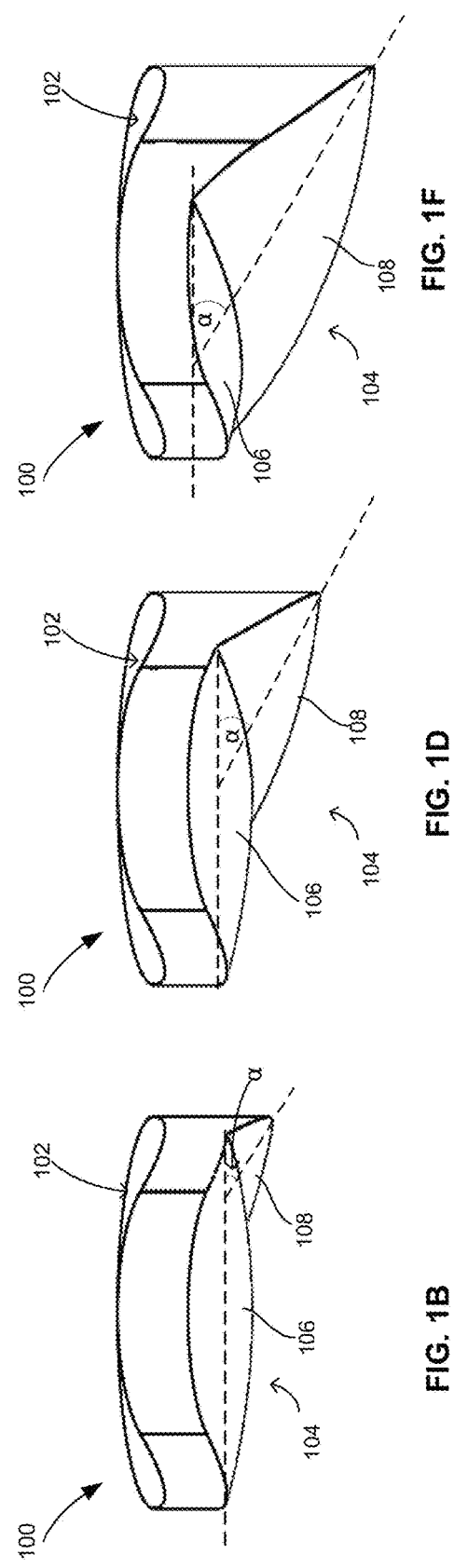

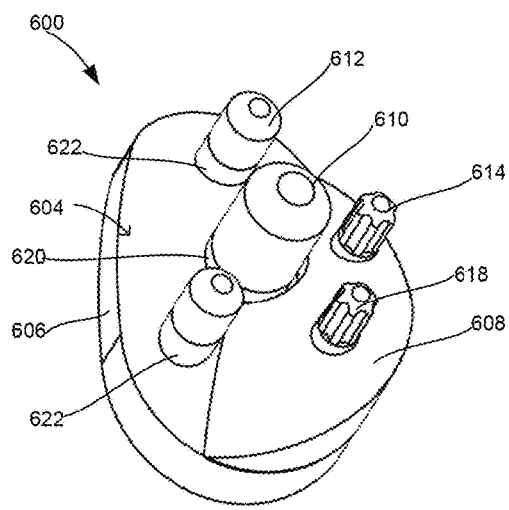
FIG. 6A
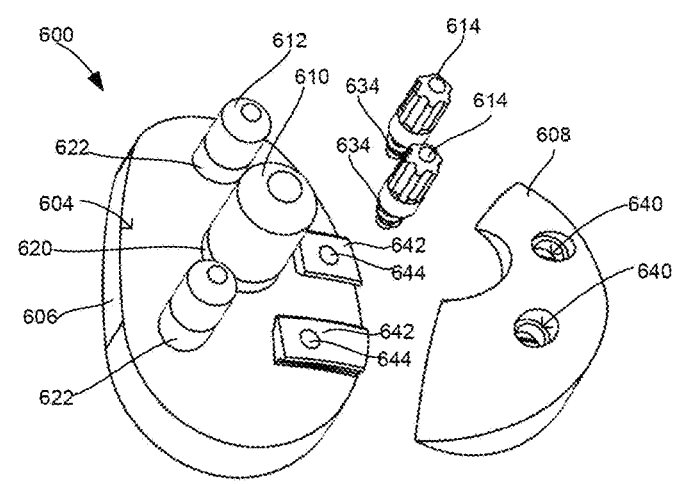
FIG. 6B
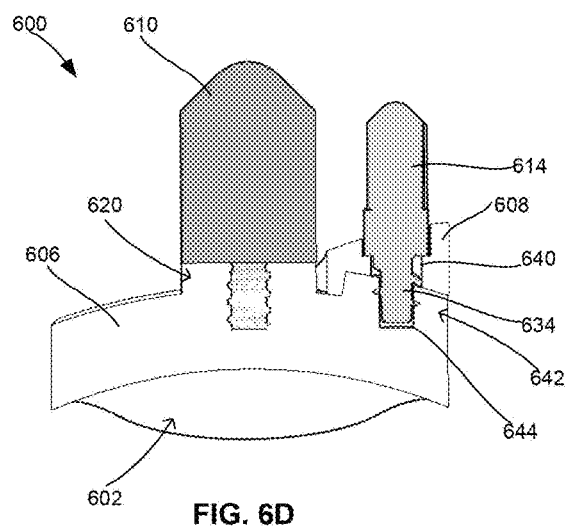
FIG. 6D
FIG. 6C

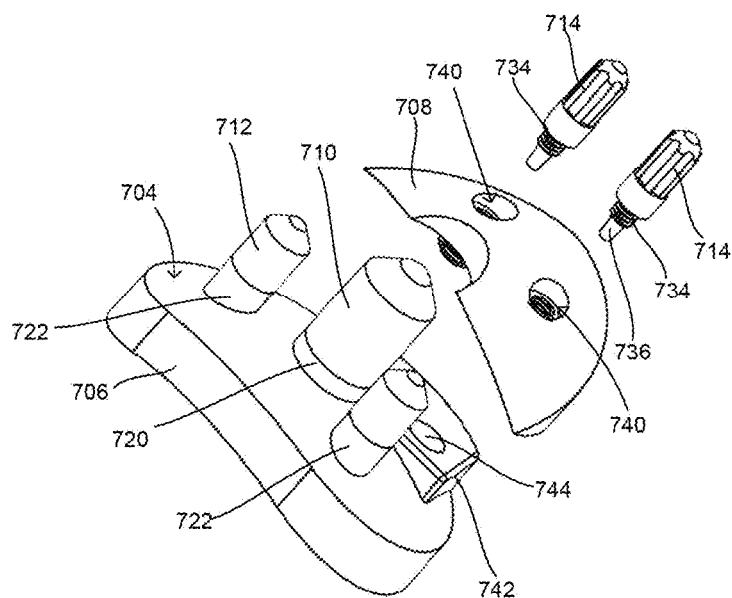
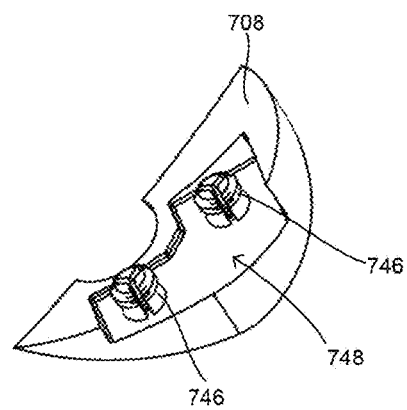
FIG. 7A
FIG. 7B
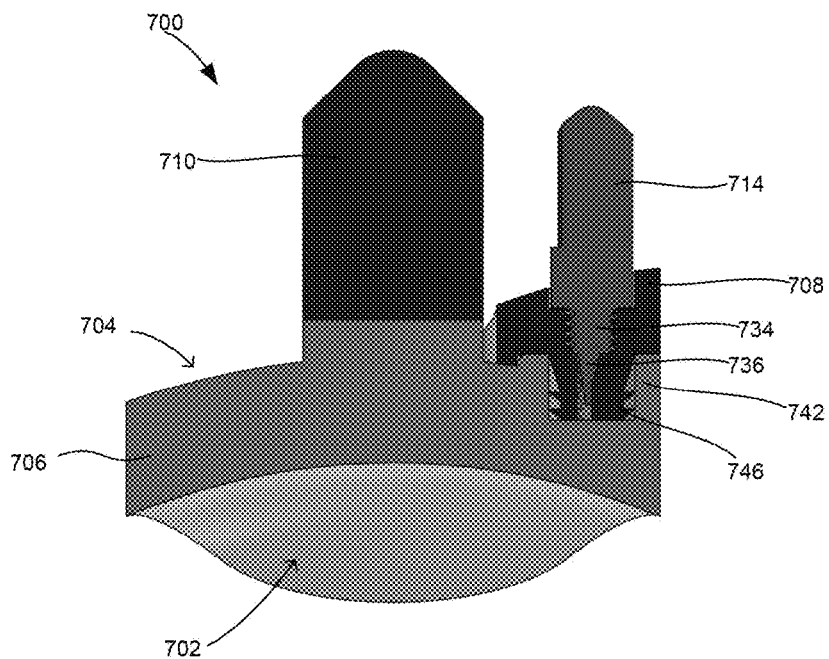
FIG. 7C

AUGMENTED GLENOID DESIGN

CROSS-REFERENCE TO RELATED APPLICATION

The present application is a divisional of U.S. patent application Ser. No. 16/925,809, filed Jul. 10, 2020, which claims the benefit of the filing date of U.S. Provisional Patent Application No. 62/873,266, filed Jul. 12, 2019, the contents of which are incorporated by reference herein.

BACKGROUND OF THE DISCLOSURE

Eccentric glenoid erosion occurs in as much as 40% of shoulder arthroplasty candidates. Wear can present anteriorly, superiorly and posteriorly, with superior being most common in reverse shoulder arthroplasty ("RSA") candidates, and posterior being most prevalent in total shoulder arthroplasty ("TSA") candidates. As the articular surface of the glenoid wears or degrades over time, the glenoid surface may take a biconcave shape. The worn or degraded portion of the glenoid may be referred to as the neoglenoid and the original portion of the glenoid may be referred to as the paleoglenoid.

Any glenoid implant that does not have a biconvex design to match the concave surface of a glenoid with eccentric glenoid erosion may require removal of a relatively large amount of bone stock, including portions of the paleoglenoid, which may be undesirable. As eccentric glenoid erosion progresses, the relative sizes and shapes of the paleoglenoid and the neoglenoid may also change. It would thus be preferably to have an augmented glenoid implant that is capable of being implanted onto a glenoid with eccentric glenoid erosion to minimize the amount of native bone stock that needs to be removed. In addition, it would be preferable to have an augmented glenoid implant or implant system that performs well when implanted onto a native glenoid with eccentric glenoid erosion. It would additionally be preferable to have an augmented glenoid implant or implant system that is suitable for use in patients with different progressions of eccentric glenoid erosion.

BRIEF SUMMARY

According to one embodiment of the disclosure, a glenoid implant may include an articulating surface, a bone contacting surface opposite the articulating surface, at least one first anchor, and at least one second anchor. The bone contacting surface may include a first portion with a first convexity configured to contact an anterior portion of the glenoid and a second portion with a second convexity configured to contact a posterior portion of the glenoid, the first convexity being different than the second convexity. The at least one first anchor may extend from the first portion of the bone contacting surface and may include a first substantially planar surface. The at least one second anchor may extend from the second portion of the bone contacting surface and may include a second substantially planar surface. The first and second substantially planar surfaces may be parallel to each other and may be substantially orthogonal to a third axis extending in a later-anterior to medial-posterior direction.

According to another embodiment of the disclosure, a glenoid implant may include an articulating surface, a bone contacting surface opposite the articulating surface, a first plurality of anchors, and a second plurality of anchors. The bone contacting surface may include a first portion with a first convexity configured to contact a first portion of the glenoid and a second portion with a second convexity configured to contact a second portion of the glenoid, the first convexity being different than the second convexity. The first plurality of anchors may extend from the first portion of the bone contacting surface along a first axis. The second plurality of anchors may extend form the second portion of the bone contacting surface along a second axis. The first and second axis may be transverse to a third axis. The third axis may extend in a lateral-anterior to medial-posterior direction.

According to a further embodiment of the disclosure, a glenoid implant may include a bearing component defining an articulating surface and an augment component. The bearing component may be comprised of a polymer. The augment component may be comprised of metal. The augment component may form at least a portion of a bone contacting surface. At least one projection may extend from the bone contacting surface.

BRIEF DESCRIPTION OF THE DRAWINGS

FIGS. 1A and 1B are perspective views of an augmented glenoid implant according to one embodiment.

FIGS. 1C and 1D are perspective views of an augmented glenoid implant with an augment different than the augment in FIGS. 1A and 1B.

FIGS. 1E and 1F are perspective views of an augmented glenoid implant with an augment different than the augments in FIGS. 1A-1D.

FIG. 6A is a perspective view of an augmented implant according to yet another embodiment.

FIG. 6B is an exploded perspective view of the augmented implant of FIG. 6A.

FIG. 6C is a perspective view of the neoglenoid portion of the augmented implant of FIG. 6A.

FIG. 6D is a cross-section of the augmented implant of FIG. 6A.

FIG. 7A is an exploded perspective view of an augmented implant according to another embodiment.

FIG. 7B is a perspective view of the neoglenoid portion of the augmented implant of FIG. 7A.

FIG. 7C is a cross-section of the augmented implant of FIG. 7A.

DETAILED DESCRIPTION

Figure 2B:
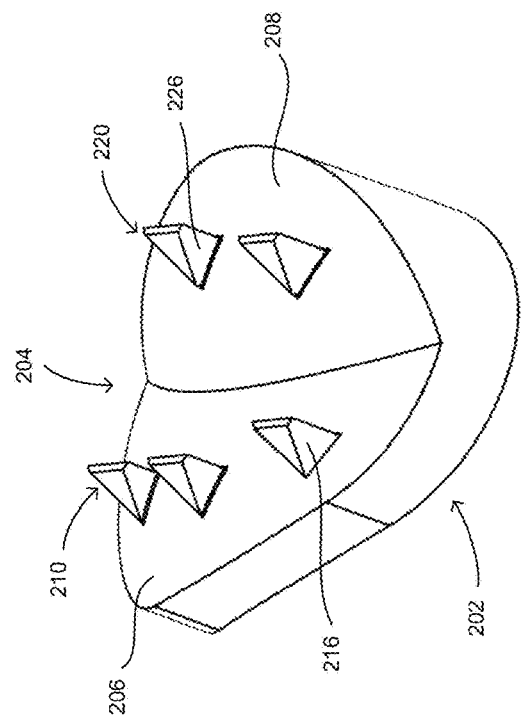
FIGS. 2B and 2C are perspective views of the augmented glenoid implant of FIG. 2A.

When referring to specific directions in the following discussion of certain implantable joint replacement devices, it should be understood that such directions are described with regard to the orientation and position of the implantable joint replacement devices during exemplary application to the human body in an intended position and/or orientation. Thus, as used herein, the term "proximal" means situated nearer to the heart of the body and the term "distal" means more situated away from the heart. The term "anterior" means towards the front part of the body or the face and the term "posterior" means towards the back of the body. The term "medial" means toward the midline of the body and the term "lateral" means away from the midline of the body. Further, as used herein, the terms "about," "generally," and "substantially" are intended to mean deviations from absolute are included within the scope of the term so modified.

FIGS. 1A-1F depict a right glenoid implant. It should be understood that a left glenoid implant may be provided that is substantially identical to the right glenoid implants described herein, although the left glenoid implants may be a substantially mirror image to the right glenoid implants described. FIGS. 1A, 1C, 1E depict side perspective views, while FIGS. 1B, 1D, 1F depict corresponding perspective views. The glenoid implant 100 has an articulating surface 102 and a bone contacting surface 104. The articulating surface 102 is intended for articulating with a corresponding humeral head of the shoulder joint, whether a native or prosthetic humeral head. The bone contacting surface 104 is intended for being in contact with the patient's glenoid upon implantation. A first portion 106 of the implant 100 is located on a generally anterior portion of implant 100. The first portion 106 has a first convexity sized and shaped to match or substantially match the concavity of the paleoglenoid. A second portion 108 of the implant 100 is located on a generally posterior portion of implant 100. The second portion 108 has a second convexity sized and shaped to match or substantially match the concavity of the neoglenoid. The convexity of the first portion 106 is different from the convexity of the second portion 108.

The different convexities of the first portion 106 and the second portion 108 results in the bone contacting surface 104 having a biconvex shape. The biconvex shape is configured to better match the degradation of the glenoid in the case of eccentric glenoid degradation that produces a neoglenoid in addition to the paleoglenoid. In such circumstances, the glenoid does not degrade evenly, thereby forming the neoglenoid and the paleoglenoid as noted above. The neoglenoid is the portion that is worn or degraded such that it becomes a secondary-articular surface formed of cortical-type bone. The portion of the glenoid that is not (or is less significantly) degraded or worn is the paleoglenoid. Thus, the biconvexity of the implant 100 allows the implant to have better contact with the eccentrically-worn glenoid upon implantation.

The first portion 106 and the second portion 108 meet or intersect at different locations on implant 100 depending on the degree or severity of degradation found in the native glenoid being replaced. For example, the glenoid implant 100 of FIGS. 1A-B has a relatively small neoglenoid component (or second portion) 108 and a relatively large paleoglenoid component (or first portion) 106 compared to the other embodiments. On the other hand, the glenoid implant 100 of FIGS. 1E-F has a relatively large neoglenoid component (or second portion) 108 and a relatively small paleoglenoid component (or first portion) 106 compared to the other embodiments. Thus, as should be understood, the glenoid implant 100 of FIGS. 1C-D has a neoglenoid component (or second portion) 108 and a paleoglenoid component (or first portion) 106 with a size generally inbetween the other two embodiments. The differences in the size and position of the neoglenoid component (or second portion) 108 may generally correspond to an increasing progression in eccentric glenoid degradation, with FIGS. 1A-B corresponding to a relatively early progression of eccentric degradation and FIGS. 1E-F corresponding to a relatively late progression of eccentric degradation. Moreover, the first portion 106 and the second portion 108 meet at an angle transverse from the anterior-posterior axis of the implant 100. In the view of FIGS. 1B, 1D, and 1F, the anterior direction generally corresponds to the left side of the page, while the posterior direction generally corresponds to the right side of the page. In one example, the angle may be about 30 degrees from the anterior-posterior axis such that the first portion 106 and the second portions 108 intersect at a 30 degree posterior bias of the neoglenoid. In some embodiments, the angle may be about 10 degrees below the anterior-posterior axis. However, it should be understood that such angles are merely exemplary, and unless noted otherwise, other angles, including angles of between about 10 degrees and about 30 degrees may be appropriate. While it is described that the first portion 106 and second potion 108 meet at an angle, that angle is descriptive of the direction of the line of intersection. The line of intersection between the first portion 106 and the second portions 108 may be a curved line that follows a typical progression of degradation, which starts posterior to the midline and moves anterior of the midline as the glenoid wears away. Thus, as noted above, FIGS. 1A and 1B depict implant 100 for instances in which there is a relatively small amount of degradation of the glenoid whereas FIGS. 1E, 1F depict implant 100 for instances in which there is a relatively large amount of degradation of the glenoid.

As depicted in FIGS. 1B, 1D, and 1F, the bone contacting surface 104 of the second portion 108 may be inclined with respect to the bone contacting surface 104 of the first portion 106. Therefore, the apex of the second portion 108 may extend past the apex of the convex bone contacting surface 104 of the first potion 106. In some embodiments, the angle of inclination a may be about 15 degrees. However, it should be understood that such an angle is merely exemplary, and unless noted otherwise, other angles, including angles of between about 5 degrees and about 30 degrees may be appropriate.

Figure 2C:
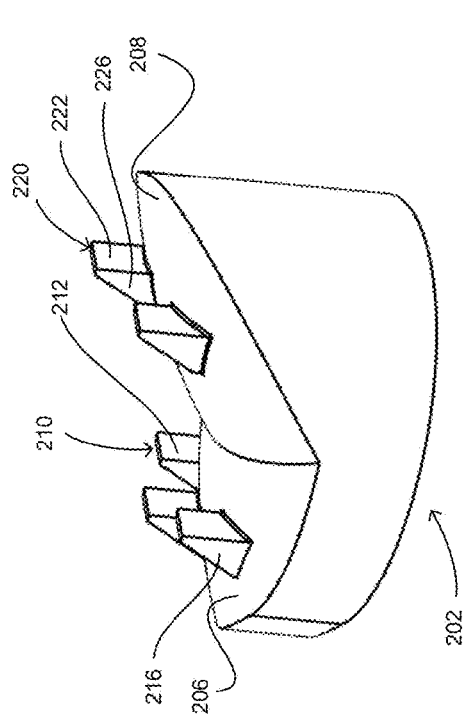
Figure 2A:
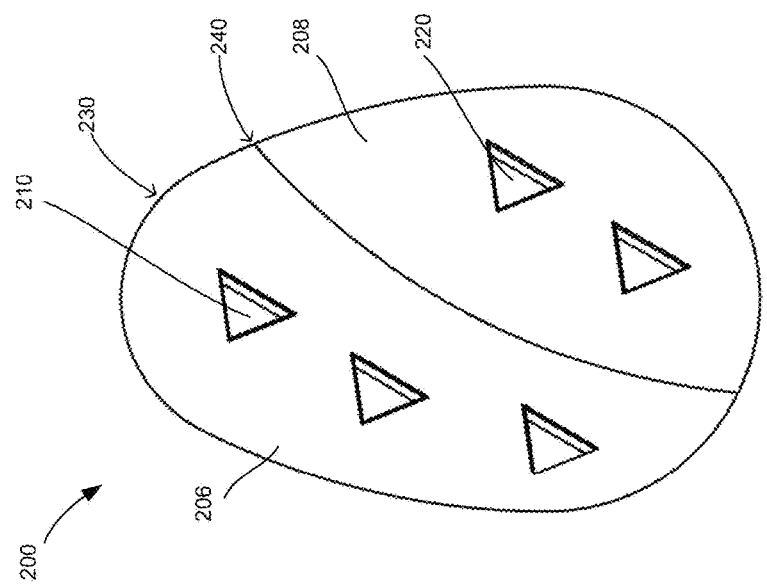
FIG. 2A is a view of the bone contacting surface of an augmented glenoid implant according to another embodiment.

FIGS. 2A and 2B depict a glenoid implant 200 having a bone contacting surface 204 and an articular surface 202. The overall shape of glenoid implant 200 is generally similar to that of glenoid implant 100 shown in FIGS. 1B-C, with the primary exception that additional fixation features are provided on the bone contacting surface 204. For example, the bone contacting surface 204 has a biconvex shape such that there is a first portion 206 with a first convexity configured to contact an anterior or paleoglenoid portion of the native glenoid and a second portion 208 with a second convexity configured to contact a posterior or neoglenoid portion of the native glenoid. The second convexity is different than the first convexity. Although only one configuration of the first portion 206 and the second portion 208 is shown, implant 200 may have different configurations in which the first portion 206 and the second portion 208 vary in size, similar to the variations shown in FIGS. 1A-1F.

Implant 200 includes a plurality of first anchors 210 and a plurality of second anchors 220 extending medially, away from the bone contacting surface 204. At least one first anchor 210 extends from the first potion 206 and at least one second anchor 220 extends from the second portion 208. For purposes of clarity, only one anchor on each the first and second portion 206, 208 is labeled in FIGS. 2A-C. In order for implant 200 to properly be seated in the glenoid, areas of bone corresponding to the anchor's size, shape, and location may be resected. Thus, where the anchors 210, 220 extend from implant 200, complementary recesses may be cut into the glenoid. The complementary recesses may be cut such that they are slightly undersized as compared to the size of the anchors 210, 220.

The glenoid may require preparation prior to the implantation of implant 200. In some instances, a surgical robot with an associated cutting tool and/or an associated computer may be programmed to form a concave curvature in the glenoid corresponding to the biconvexity of implant 200. Further, a robot may be used to precisely resect the glenoid to create recesses that are complementary to the anchors 210, 220 of implant 200. Use of a robot may provide for greater precision, compared to manual preparation of the bone, in the size, shape, and location of the resected bone as the robot can be programmed to perform the resection based on data provided by scans of the patient. For example, the patient's glenoid may be imaged via any suitable modality, such as MRI or CT scanning, and the data acquired from the scanning may be manipulated to create a surgical plan to precisely resect the patient's glenoid to have the desired shape to receive the implant 200. The shape and/or geometry of the particular implant 200 may also be uploaded to the surgical system to assist in the planning. The surgical plan may be fed to a robotic surgical system and may be implemented by the robotic surgical system, with or without assistance by a surgeon.

As shown in FIGS. 2A-2C, anchors 210, 220 have a wedge like shape. First anchor 210 has a substantially planar surface 212 and second anchor 220 has a substantially planar surface 222. Substantially planar surfaces 212, 222 may be parallel or substantially parallel to one another and extend away from the bone contacting surface traverse to an axis in a lateral-anterior to medial-posterior direction. The axis that lies in the lateral-anterior to medial-posterior direction can be considered a "slip plane," described in greater detail below.

Figures 3A, 3B, 3C:
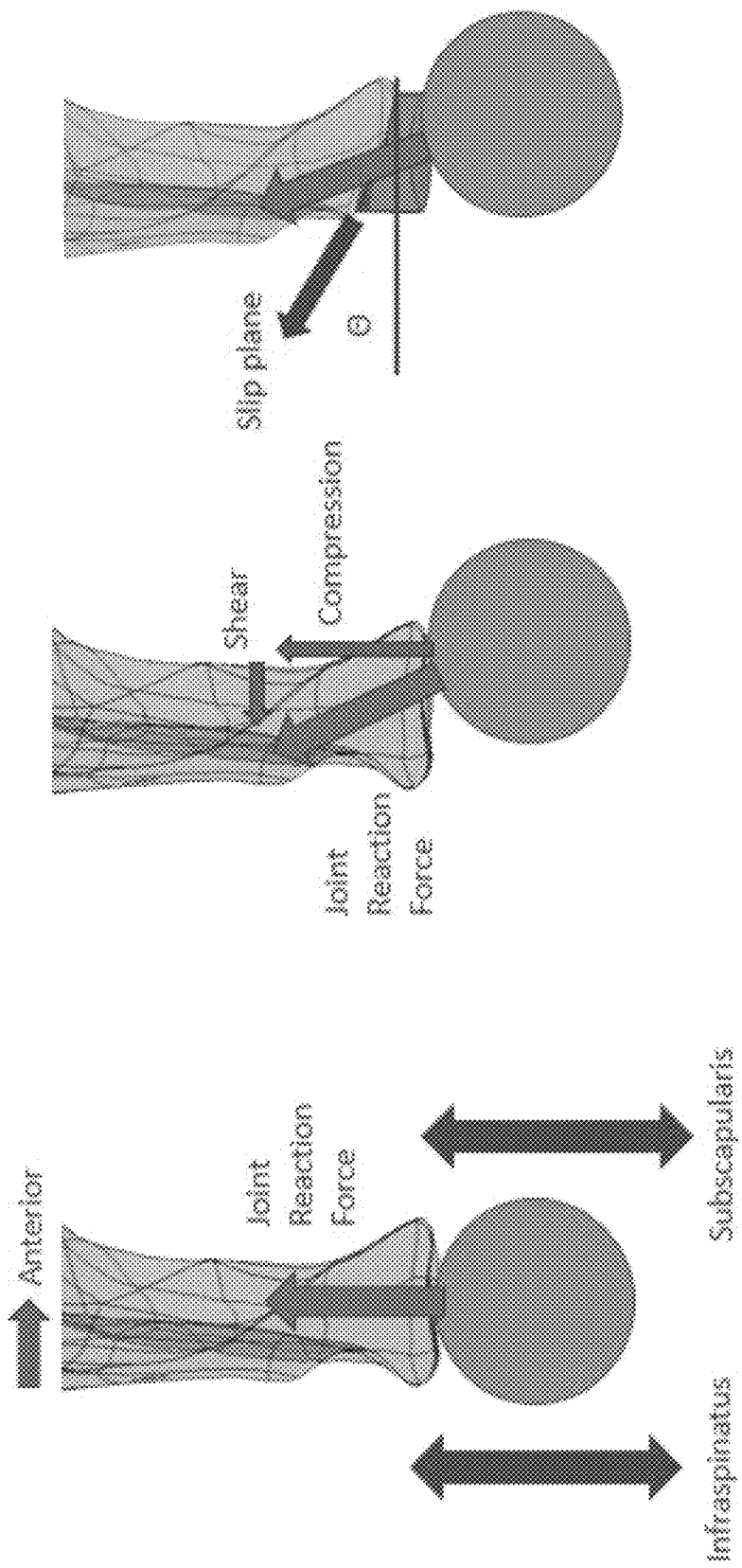
FIGS. 3A-3C are a series of force diagrams depicting forces exerted on the shoulder from a superior-to-inferior view.

The slip plane is created as a result of the compression force and shear force exerted on the bone when implant 200 is implanted. FIGS. 3A-C depict force diagrams on a representative right glenoid. The portion of the bone shown in FIGS. 3A-C is a view of the right shoulder in a superior to inferior direction (i.e. looking down from above the shoulder). A representative humeral head of the shoulder joint is shown in FIGS. 3A-C as a circular member that interacts with, and applies forces to, the glenoid of the shoulder joint. The anterior direction is shown in FIG. 3A. The joint reaction force is exerted on the glenoid in the medial direction in a normal, neutral state, with the glenoid and associated soft tissue, such as the infraspinatus and subscapularis muscles, helping to maintain the humeral head in contact with the glenoid. FIG. 3B illustrates the humeral head in an anterior position relative to the glenoid, which may be a typical position during typical use of the shoulder. In this edge-loaded state, compression force is applied to the glenoid in the medial direction and a shear force is applied to the glenoid in the posterior direction, for example as a result of soft tissue tending to push the humeral head to the neutral position shown in FIG. 3A. Therefore, the resultant force (i.e. the combination of the compression force and the shear force) in the edge-loaded state is the joint reaction force exerted on the bone at an angle in the posterior-medial direction.

FIG. 3C illustrates a humeral head in an edge-loaded state, similar to FIG. 3B, with the exception that the glenoid shown in FIG. 3C has eccentric erosion with an augmented glenoid implant, similar to implant 100 and/or implant 200, implanted thereon. The posterior-medial directed force exerted on the augmented glenoid by the edge-loaded humeral head tends to cause the augmented glenoid implant to want to slip or move along the slip plane illustrated in FIG. 3C, which may be generally aligned with the surface of the neoglenoid. In other words, when implant 200 is implanted on the bone, during typical movement of the shoulder joint, the resultant joint reaction force may create a potential for implant 200 to slip along the bone, thereby creating a "slip plane." The slip plane effectively bisects the line of intersection of the neoglenoid and paleoglenoid and lies in a plane tangential to the bone contacting surface of the neoglenoid portion of the implant.

Referring back to FIGS. 2A-C, substantially planar surfaces 212, 222 are substantially orthogonal to the axis of the slip plane to assist in the prevention of implant 200 from slipping. As the joint reaction force is exerted on implant 200, for example during edge loading, substantially planar surfaces 212, 222 will exert a force on the area of resected bone within which the anchors 210, 220 are implanted. The substantially planar shape of surfaces 212, 222 creates a relatively large amount of surface area of contact with the glenoid, which further assists in preventing slipping along the slip plane. The force exerted by the substantially planar surfaces 212, 222 and the reaction force experienced by the anchors 210, 220 will thus tend to prevent the implant 200 from slipping along the slip plane.

The shape of the anchors 210, 220 allow for size of the anchors to be minimized without compromising function. As should be understood, there is generally a desire to maintain the most amount of healthy bone stock when implanting a prosthesis onto the bone, but it is also important to provide sufficient fixation of the implant. These two considerations may be at odds with each other. For example, increased fixation is typically achieved by increasing the size of anchors, which necessarily would require increasing the amount of healthy bone stock removed. With a wedge shape, anchors 210, 220 are tapered in various directions to minimize the volume or size of the anchor while still maintaining their ability to sufficiently affix the implant 200 to the glenoid under normal loading conditions. Anchor surfaces 216 and 226 may have a substantially triangular shape. That is, anchor surface 216 (or 226) has a first width at a portion of anchor 210 (or 220) closest to the bone contacting surface 204 and a second width, smaller than the first width, at a portion spaced away from the bone contacting surface 204. The portion spaced away from the bone contacting surface may be the apex of anchor 210 (or 220). The first width, closest to the bone contacting surface 204, tapers to the second width, thereby creating the triangular shape of anchor surface 216 (or 226). As should be understood, each first anchor 210 may have a shape that is similar or identical to the shape of each second anchor 220.

Each first anchor 210 and each second anchor 220 may include a taper along the slip plane. As best seen in FIG. 2A, the base of the anchors 210, 220 has a substantially triangular shape. The base of the anchor is located at the point where anchor 210, 220 meets bone contacting surface 204. With the triangular shape of the base of anchors 210, 220, the anchors have a first width at a posterior portion of the base of the anchor and a second width at an anterior portion of the base of the anchor 210, the second width being smaller than the first width. The first width tapers to the smaller second width along an axis parallel or substantially parallel to the slip plane.

The placement and/or location of anchors 210, 220 along bone contacting surface 204 contributes to the ability of the anchors 210, 220 to help resist potential slipping. One of the first anchors 210 from the first portion 206 of implant 200 may align with a corresponding one of the second anchors 220 from the second portion 206 of implant 200 along an axis that is parallel or substantially parallel to the axis of the slip plane. However, in some embodiments, first anchors 210 from the first portion 206 may not align with any of the second anchors 220 from the second portion. The placement of anchors 210, 220 on their own or in conjunction with the substantially planar surfaces 212, 222 extending away from the bone contacting surface 204 traverse to the axis of the slip plane may provide for greater stability of implant 200. As shown in FIGS. 2A-2C, first portion 206 includes three anchors 210 and second portion 208 includes two anchors 220. However, in alternative embodiments, the number of anchors in each the first and second portions 206, 208 may vary. For example, the paleoglenoid or first portion 206 may include one, two, three, or more first anchors 210, and the neoglenoid or second portion 208 may include one, two, three, or more second anchors 220.

It may be preferable that, when implant 200 is implanted onto the patient's glenoid, the anchors 210, 220 are located in an area of the glenoid with the greatest bony strength, such as close to the cortical wall. The cortical wall and the cancellous bone immediately below the cortical wall generally have the greatest bone density, or strength. The cancellous bone in the middle of the metaphysis, in this case the glenoid vault, generally, has the least bone density, or strength. Therefore, placing anchors 210, 220 at a location at or near the transition point from the neoglenoid to the paleoglenoid may result in less effective anchoring since that location is typically comprised of weak cancellous bone. If during preparation for implant 200 the cortical bone of the neoglenoid and paleoglenoid is preserved, the anchors 210, 220 are configured to extend, at least, through the cortical surface. Thus, according to some embodiments, the bone contacting surface 204 has an outer perimeter 230 and a transition line 240 where the first portion 206 and second portion 208 meet. The transition line may be a curved line. The first anchor 210 may be positioned at a first distance from both the outer perimeter edge 230 and the transition line 240, such that the first anchor 210 is substantially in the middle of the first portion 206 (i.e. at a distance between the perimeter and the transition line). The second anchor 220 may similarly be positioned at a second distance from both the outer perimeter edge and the transition line, such that the second anchor 220 is substantially in the middle of the second portion 208 (i.e. at a distance between the perimeter and the transition line). In some instances, the anchors 210, 220 are located at a position in the first and second portions 206, 208, respectively, that is substantially the same distance from the nearest cortical shell or perimeter edge.

Figure 4A:
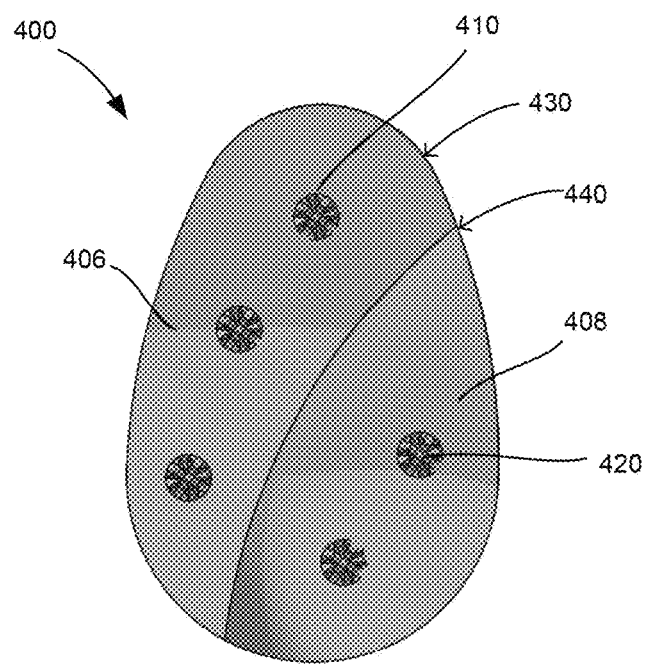
FIG. 4A is a view of the bone contacting surface of an augmented glenoid implant according to a further embodiment.
Figure 4B:
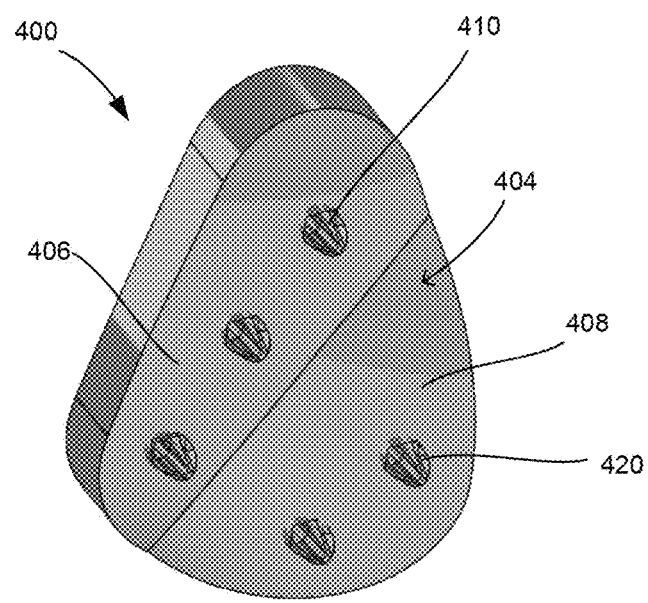
FIG. 4B is a perspective view of the augmented implant of FIG. 4A.

FIGS. 4A and 4B depict another embodiment of implant 400, substantially similar to implant 200. Implant 400 may be substantially similar or identical to implant 200, including the variations described in connection with implant 200, with the main exception that implant 400 includes a different anchoring or fixation system than implant 200. The bone contacting surface 404 has a biconvex shape such that there is a first portion 406 with a first convexity configured to contact an anterior or paleoglenoid portion of the glenoid and a second portion 408 with a second convexity configured to contact a posterior or neoglenoid portion of the glenoid. The second convexity is different than the first convexity. Although only one configuration of the first and second portions 406, 408 is shown, implant 400 may have different configurations in which the first and second portions 406, 408 vary in size and convexity, similar to the variations shown in FIGS. 1A-1F.

A plurality of first anchors 410 and second anchors 420 extend from the bone contacting surface 404. At least one anchor 410 extends from the first potion 406 and at least one anchor 420 extends from the second portion 408. The anchors 410, 420 extend away from the bone contacting surface. For purposes of clarity, only one anchor on each the first and second portion 406, 408 is identified in FIGS. 4A-B. In order for implant 400 to properly be seated in the glenoid, areas of bone corresponding to the anchor's size, shape, and location may be resected in the native glenoid. Thus, where the anchors 410, 420 extend from implant 400, complementary recesses may be cut into the glenoid, as described in detail above.

As compared to the anchors 210, 220 of implant 200, anchors 410, 420 of implant 400 are substantially bullet shaped. Bullet shaped anchors may have a first base portion closest to bone contacting surface 404 that is substantially cylindrical with a first radius and a second tip portion being spaced away from bone contacting surface 404. The first portion is a cylindrical or substantially cylindrical body and the second portion is a tapered head or tip portion. The tapered tip portion may be hemispherical or it may be conical, with or without a sharp pointed tip. In some embodiments, a conical top portion tapers along a longitudinal axis of the anchor for a certain distance and then has a domed or flat apex. Alternatively, bullet shaped anchors may have a tapering body with pointed edges in the shape of a cross or starburst, dependent upon how many edges there are. Moreover, the bullet shaped anchors may have a combination of shapes, such that the anchor has a cylindrical body with a tapering head or top portion that includes pointed edges in the shape of a cross or starburst. In some embodiments, the bullet shape of the anchors 410, 420 may be general similar to the shape of a Phillips head (or crosshead) screwdriver, with alternating flutes and recesses forming a general cross shape. The different shapes of anchors 410, 420 described above are not meant to be limiting. They are merely exemplary as the bullet shaped anchors can take a variety of shapes.

The configuration and positioning of the anchors 410, 420 is substantially similar to those of anchors 210, 220. One of the first anchors 410 from the first portion 406 of implant 400 may align with a corresponding one of the second anchors 420 from the second portion 406 of implant 400 along an axis that is parallel or substantially parallel to the axis of the slip plane. As shown in FIGS. 4A and 4B, first portion 406 includes three anchors 410 and second portion 408 includes two anchors 420. The location and reason for the positioning of anchors 410, 420 is substantially similar to the reasons discussed above with respect to anchors 210, 220.

Figure 5A:
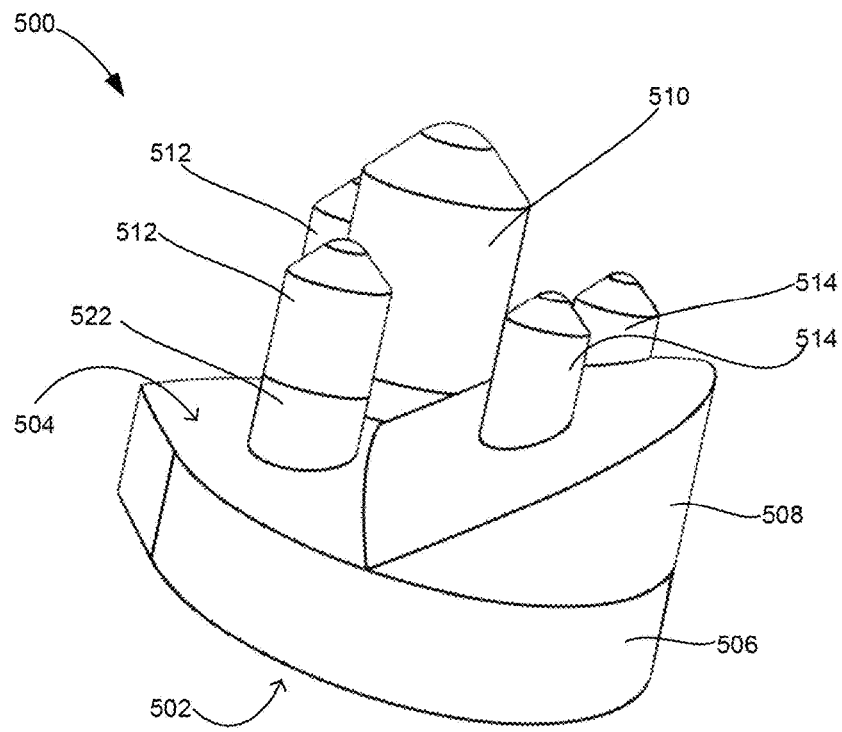
FIG. 5A is a perspective view of an augmented implant according to yet a further embodiment.
Figure 5B:
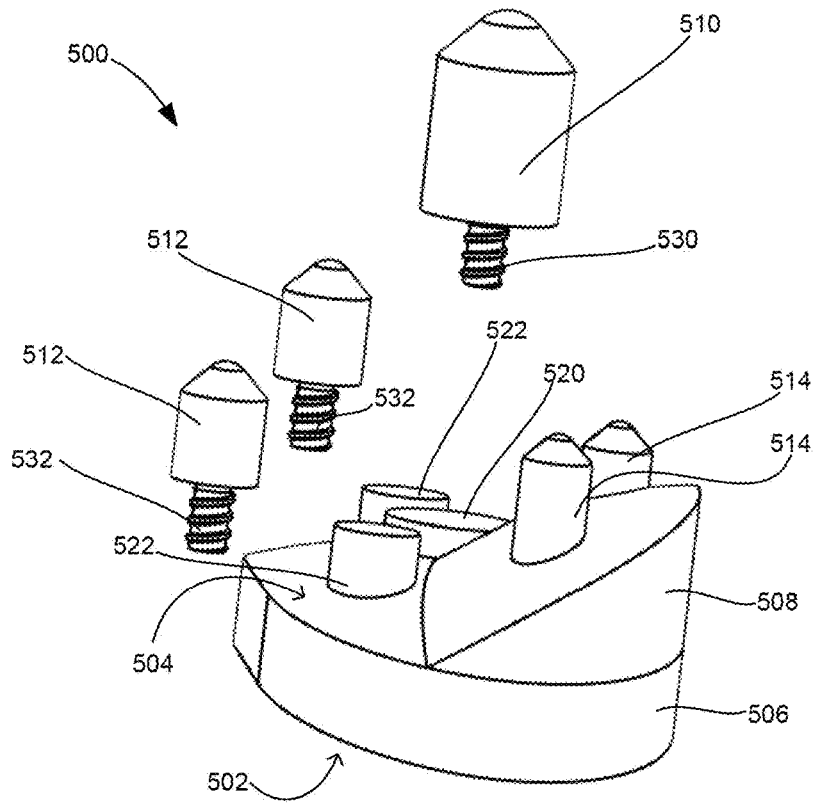
FIG. 5B is an exploded perspective view of the augmented implant of FIG. 5A.

FIGS. 5A and 5B depict another embodiment of an augmented glenoid implant. Implant 500 has an articulating surface 502 and a bone contacting surface 504. The bone contacting surface 504 has a biconvex shape and may be comprised of two different portions. The bearing component 506 of implant 500 defines the articulating surface 502 and has an opposing bone contacting surface 504 surface having a first convexity sized and shaped to match or substantially match the concavity of the paleoglenoid. An augment 508 of implant 500 has a bearing contacting surface and an opposing bone contacting surface having a second convexity sized and shaped to match or substantially match the concavity of the neoglenoid. The bearing component 506 in combination with augment 508 creates a complete bone contacting surface 504. The bearing component 506 may be formed of a biocompatible polymer and augment 508 may be formed of a biocompatible metal. The metal may be porous, such as a porous titanium, to enhance bone ingrowth into the porous metal.

Augment 508 may be a molded inlay. Thus, bearing component 506 may be overmolded on augment 508. In other words, the bearing component 506 may be formed from an injection molding type of process in which the material that will form the bearing component is placed in a mold (or similar device) in a soft or liquid state and allowed to harden or solidify on the augment 508 to form the desired composite shape. The bearing contacting surface of augment 508 may include a pattern that allows for a better bond or adhesion to the bone contacting surface 504 of bearing component 506, particularly during the molding process. The pattern may be etched into, engraved into, or built into augment 508, for example in the case of additive manufacturing of the augment 508. The pattern may be a waffle pattern or any other mesh type pattern that may enhance the bond between augment 508 and bearing component 506.

Augment 508 may include at least one anchor or peg 514 extending from bone contacting surface 504. As shown in FIG. 5A, augment 508 may include two pegs 514 extending from bone contacting surface 504. Pegs 514 are intended to stabilize the augment against the neoglenoid cortical wall. Pegs 514 may be integral to augment 508 such that augment 508 and pegs 514 are provided as a single piece, for example during additive manufacturing. Thus, pegs 514 may also be comprised of biocompatible metal, such as titanium, and may be a porous metal (including porous titanium) to allow for enhanced bone ingrowth into augment 508.

Pegs 514 may have various shapes, including a bullet shape like anchors 410, 420. Bullet Pegs 514 may have a first portion closest to bone contacting surface 504 that is substantially cylindrical with a first radius and a second tapered, conical, or frustoconical portion extending from the first portion and being spaced away from bone contacting surface 504. Although shown as conical, the tapered tip of the second portion may have other shapes, such as hemispherical. In some embodiments, the conical or frustoconical tip portion tapers along a longitudinal axis of the anchor for a certain distance and then has a domed or flat apex.

One or more pegs may also extend from the bone contacting surface 504 of the bearing component 506. In the illustrated embodiment, these pegs include a center peg 510 and two peripheral pegs 512, although other numbers and positions of these pegs may be suitable. Center peg 510 may include a base 520 and a body portion. Similarly, peripheral pegs 512 may each include a base 522 and a body portion. Bases 520, 522 may be substantially cylindrical and extend along an axis transverse to bone contacting surface 504. The bases 520, 522 may be formed of a polymer and, therefore, may be integral with bearing component 506. In other words, the bearing component 506, and bases 520, 522, may be molded as a single monolithic member and formed of a polymer with the rest of bearing component 506. The body portions of pegs 510, 512 may be substantially cylindrical. The body portions of pegs 510, 512 may extend a distance along a longitudinal axis of the pegs 510, 512 before tapering from a first width to a smaller second width, such that the tip portion of the body is conical, frustoconical, or otherwise tapered. However, in some embodiments, the tip portion of the body of pegs 510, 512 may be hemispherical, or have a taper with pointed edges in the shape of a cross or starburst, similar to the bullet shape of anchors 410, 420. The body portions of pegs 510, 512 may be formed of a biocompatible metal, such as titanium, and may be a porous metal, including porous titanium, to allow for enhanced bone ingrowth into the body portions of the pegs 510, 512.

Center peg 510 may be located substantially in the center of implant 500, for example a substantially equal distance between the superior and inferior ends of the implant 500, and a substantially equal distance between the anterior and posterior ends of the implant 500. Thus, augment 508 may be shaped to have a recess or cut out sized and shaped to accommodate center peg 510. Although FIGS. 5A-B illustrate bearing component 506 as including two peripheral pegs 512, bearing component 506 may include one peripheral peg 512, three or more peripheral pegs 512, or in some embodiments, no peripheral pegs 512. Center peg 510 and peripheral pegs 512 are removably coupled to bases 520 and 522, respectively.

Pegs 510, 512 have a coupling component 530, 532, respectively, extending from the body portion of pegs 510, 520. In an embodiment in which the coupling component is a threaded protrusion, as shown in FIG. 5B, bases 520, 522 may have a complementary threaded aperture for receiving the corresponding coupling component 530, 532 therein. However, in alternative embodiments, coupling components 530, 532 may have a press fit connection, interference fit, or any other suitable connection mechanism with bases 520, 522. The polymeric bases 520, 522 of bearing component 506 may assist in performing a revision procedure to remove implant 500 during a later procedure. For example, compared to metal components that have had bone ingrowth occur, the polymer material may be relatively easily cut away with a tool, such that the bases 520, 522 could be relatively easily cut and removed from the metal augment 508 component and the metal body portions of pegs 510, 512, with the metal portions being more precisely removed from the bone after the polymer portions of implant 500 are cut away. In this scenario, the amount of bone stock that would need to be removed in a revision procedure may be minimized or otherwise reduced.

FIGS. 6A-6D depict a glenoid implant 600 similar to implant 500, however the augment component 608 is modular such that the augment component 608 is removably coupled to the bearing component 606. Implant 600 has an articulating surface 602 for articulating with a humeral head, and a bone contacting surface 604 generally opposite the articulating surface 602. In an assembled condition, the bone contacting surface 604 has a biconvex shape and is comprised of two different portions. The bearing component 606 of implant 600 defines the articulating surface 602 and has an opposing bone contacting surface 604 surface having a first convexity sized and shaped to match or substantially match the concavity of the paleoglenoid. An augment 608 of implant 600 has a second convexity sized and shaped to match or substantially match the concavity of the neoglenoid. The bearing component 606 may be formed of a biocompatible polymer and the augment portion 608 may be formed of a biocompatible metal, including porous metals such as porous titanium.

The pegs 610, 612 extending from bearing component 606 may each include a base 620, 622 and a body portion extending from the base. Pegs 610, 612 may be substantially similar or identical to corresponding pegs 510, 512 of implant 500 and are thus not described in greater detail herein.

Augment component 608 may be generally similar to augment component 508 of implant 500, with the main exception that it is a modular component of implant 600. To couple augment 608 to bearing component 606, at least one dovetail connection platform 642 extends from bearing component 606. In the embodiment shown in FIG. 6B, bearing component 606 includes two dovetail connection platforms 642. The dovetail connection platforms may be relatively narrow nearer bone contacting surface 604, and relatively wide at a spaced distance from bone contacting surface 604. As seen in FIG. 6C, augment 608 includes corresponding recesses 646 configured to receive the dovetail connection platforms 602. Recesses 646 may have complementary shapes to the dovetail connection platforms 642 so that, after the augment component 608 is slid over the dovetail connection platforms 642, the augment component 608 may not be disconnected from the bearing component 606 by simply lifting the augment component 608 away from the bearing component 606. Augment 608 is slidably coupled to bearing component 606 via the one or more dovetail connection platforms 642. In other words, the augment 608 may include two recesses having complimentary shapes to the doevetail connection platforms 642 so that, after the augment is slid over the dovetail connection platforms 642, the augment component 608 cannot be disconnected from the bearing component 606 by simply lifting the augment component 608 away from the bearing component 606. In one embodiment, each dovetail connection platform 642 may be formed as a monolithic structure with the remainder of bearing component 606, such as by molding.

Each dovetail connection platform 642 includes an aperture 644 that aligns with throughbores 640 on augment 608 when augment 608 is slidably coupled with bearing component 606. Throughbores 640 are generally cylindrical and sized to receive pegs 614, or portions thereof. Throughbores 640 may include a shoulder or step that creates a portion of throughbore 640 having a smaller diameter than pegs 614. The shoulder or step may be used as a stopping mechanism to ensure that pegs 614 are not inserted too far or to ensure that pegs are fully inserted.

Pegs 614 are not integral to augment 608. Pegs 614 are intended to stabilize the augment against the neoglenoid cortical wall by acting as an anchor as well as a coupling mechanism to further secure the augment component 608 to the bearing component 606. Pegs 614 provide a coupling mechanism for augment 608 and bearing component 606, in addition the dovetail connection. In other words, while the dovetail connection prevents the augment component 608 from lifting off of the bearing component 606, the pegs 614, when coupled to the bearing component 606 through the augment component 608, prevent the augment component 608 from sliding relative to the bearing component 606. Pegs 614 may be formed of biocompatible metal, such as titanium, and may be a porous metal, including porous titanium, to provide for enhanced bone ingrowth.

Pegs 614 may take any shape of the other pegs described herein. In the illustrated embodiment, pegs 614 are generally cylindrical with a body and a coupling portion 634. The body portion comprises a generally solid portion, such that there is a smooth surface, and a portion with pointed edges creating the shape of a cross or starburst. The portion with pointed edges creating the shape of a cross or starburst may facilitate a user gripping the pegs 614 in order to manually rotate the pegs 614 to couple augment 608 to bearing component 606, although a tool could alternatively be used to rotate the pegs 614. Coupling portion 634 of pegs 614 includes a threaded protrusion in the illustrated embodiment, with apertures 644 on dovetail connection platforms 642 having corresponding threaded portion to receive coupling portion 634. However, it should be understood that other types of connections, such as press fits and interference fits, may be suitable instead. Thus, when augment 608 is slidably received by the dovetail connection platforms 642 on bearing component 606, pegs 614 are inserted into throughbores 640 and screwed into apertures 644. This provides for a tight connection and positive location of augment 608 against bearing component 606.

According to some embodiments, apertures 644 of dovetail connection platform 642 may not have corresponding threads to match coupling portion 634. In such embodiments, coupling portion 634 may self-tap into the polymer of the aperture 644 thereby creating a threaded connection. Also, although a dovetail connection is shown to connected augment 608 to bearing component 606, other geometrical configurations, such as rails, grooves, etc. may be suitable instead of dovetails.

FIGS. 7A-7C depict a modular glenoid implant 700 similar to implant 600. Implant 700 has an articulating surface 702 and a bone contacting surface 704. When implant 700 is assembled, the bone contacting surface 704 has a biconvex shape and is comprised of two different portions. The bearing component 706 of implant 700 defines an articulating surface 702 adapted to articulate with a humeral head, and has an opposing bone contacting surface 704 surface having a first convexity sized and shaped to match or substantially match the concavity of the paleoglenoid. An augment 708 of implant 700 has a second convexity sized and shaped to match or substantially match the concavity of the neoglenoid. The bearing component 706 may be formed of a biocompatible polymer and the augment component 708 may be formed of a biocompatible metal. The metal may be porous, such as porous titanium, to provide for enhanced bone ingrowth.

The pegs 710, 712 extending from bearing component 706 include a base 720, 722 and a body portion. Pegs 710, 712 may be substantially similar or identical to pegs 610, 612 and/or pegs 510, 512, and are thus not described in greater detail herein.

Augment 708 is a modular component of implant 700. To couple augment 708 to bearing component 706, a protrusion or platform 742 extends from bearing component 706. Platform 742 is preferably integral with bearing component 706. Platform 742 may include apertures 744 configured to receive a protrusion and/or collet portion 746 of augment 708, as described below.

Augment 708 includes a corresponding recess 748 configured to receive platform 742. Augment 708 further includes bores 740, which align with apertures 744 on platform 742 when platform 742 is received by the recess in augment 708. Extending from augment 708 along the longitudinal axis of bores 740 are protrusions or collets 746. Bores 740 at least partially extend through collets 746. Bore 740 has a first diameter at a portion closest to bone contacting surface 704. A shoulder or step may be included within bore 740, thereby creating a smaller diameter for the remainder of the bore. The portion of the bore with the smaller diameter may include threads that match a threaded portion 734 of set screw, peg, protrusion, or anchor 714. Set screws 714 are of a longitudinal length that allows the set screws to act as an anchor, peg, or protrusion.

The set screws 714, as shown, are not integral to augment 708. However, in some embodiments, at least one set screw 714 may be integral with augment 708. Set screws 714 are intended to stabilize the augment against the neoglenoid cortical wall and provide a coupling mechanism for augment 708 and bearing component 706. Set screws 714 may be formed of biocompatible metal, such as titanium, and may be a porous metal, including porous titanium, to provide for enhanced bone ingrowth.

Set screws 714 may be generally cylindrical with a body, a coupling portion 734, and a drive portion 736. The body portion may be a generally solid portion, such that there is a smooth surface, and a portion with pointed edges creating the shape of a cross or starburst. Like pegs 614, the portion with pointed edges creating the shape of a cross or starburst may facilitate a user in gripping the set screws 714 such that set screws 714 can be rotated and screwed into threads to couple to the bearing component 706. Coupling portion 734 of set screws 714 includes a threaded portion. A portion of bore 740 includes corresponding threads to receive coupling portion 734. Thus, when platform 742 is received in the recess of augment 708, set screws 714 are inserted into bores 740 and tightened, effectively coupling the set screws 714 and augment 708. This provides for a tight connection and positive location of augment 708 against bearing component 706.

Driving portion 736 may be a tapered conical shape. The driving portion 736 tapers along the longitudinal axis of set screw 714. Driving portion is the leading portion inserted into bore 740. Driving portion 736 passes through bore 740 and into collet 746 of augment 708. As set screw 714 is threadably coupled to augment 708, driving portion 736 extends further into collet 746 such that collet 746 expands or spreads radially. The expansion of collet 746 causes a press-fit or friction-fit interference between collet 746 and bearing component 706. This fit provides a high degree of strength between the metal augment 708 and polymer bearing component 706. In some instances, the metal collet 746, when expanded, will be driven into the polymer bearing component 706 thereby coupling augment 708 to polymer component 706.

As noted above, implants 600, 700 include modular components, such that augments 608, 708 can be interchanged with a similarly designed augment having a different size and/or convexity. This may allow users to choose the augment that will best suit the needs of a particular patient. For example, if there is a large amount of wear or degradation, such that the concavity of the neoglenoid is large, an augment having a large convexity matching or substantially matching the concavity may be provided. This allows for a more patient specific fit.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A glenoid implant, comprising:
   a bearing component defining an articulating surface and at least a first portion of a bone contacting surface, wherein the bearing component is comprised of a polymer and includes a platform;
   an augment component, wherein the augment component is comprised of a metal, the augment component forming at least a second portion of the bone contacting surface, wherein the augment component comprises a corresponding recess configured to receive the platform; and
   at least one projection extending from the bone contacting surface, wherein when the at least one projection is inserted into at least one throughbore of the augment component and at least one aperture of the platform, the at least one projection to secures the augment component to the bearing component,
   wherein the at least a first portion of the bone contacting surface has a first convexity and the at least a second portion of the bone contacting surface has a second convexity, the first convexity being different from the second convexity.

2. The implant of claim 1, wherein the at least one projection is comprised of a porous metal.

3. The implant of claim 1, wherein the at least one projection includes a polymer base portion integral with the bearing component, the base portion positioned adjacent a tip portion of the at least one projection.

4. The implant of claim 1, wherein the bearing component is overmolded on the augment component.

5. The implant of claim 1, wherein the augment component forms in combination with the bearing component the bone contacting surface.

6. The implant of claim 1, wherein the augment component is removably coupled to the bearing component.

7. The implant of claim 6, wherein the bearing component includes at least one dovetail connection platform extending from the bearing component and the augment component includes a corresponding recess configured to receive the at least one dovetail connection platform.

8. The implant of claim 7, wherein the augment component includes at least one throughbore and the at least one dovetail connection platform includes an aperture such that when the augment component is coupled to the bearing component, the at least one throughbore aligns with the aperture.

9. The implant of claim 8, wherein when the augment component is coupled to the bearing component, the at least one projection is configured to be inserted into the at least one throughbore and the aperture to secure the augment component to the bearing component.

10. The implant of claim 9, wherein the at least one projection includes a threaded protrusion.

11. The implant of claim 10, wherein the aperture is a threaded aperture such that when the at least one projection is inserted through the at least one throughbore and into the aperture the at least one projection is threadably coupled to the bearing component.

12. The implant of claim 10, wherein when the at least one projection is inserted through the at least one throughbore and into the aperture, the threaded portion self-taps into the aperture to threadably couple the at least one projection to the bearing component.

13. The implant of claim 1, wherein when the augment component is coupled to the bearing component, the at least one throughbore aligns with the at least one aperture.

14. The implant of claim 1, wherein the at least one projection includes a threaded protrusion.

15. The implant of claim 14, wherein the at least one aperture is a threaded aperture such that when the at least one projection is inserted through the at least one throughbore and into the at least one aperture the at least one projection is threadably coupled to the bearing component.

16. The implant of claim 14, wherein when the at least one projection is inserted through the at least one throughbore and into the aperture, the threaded portion self-taps into the aperture to threadably couple the at least one projection to the bearing component.

17. The glenoid implant of claim 1, wherein the first convexity is configured to contact an anterior portion of the glenoid and the second convexity is configured to contact a posterior portion of the glenoid.

18. The glenoid implant of claim 1, wherein the at least one protrusion is a set screw.

19. The glenoid implant of claim 1, further comprising at least one collet extending from the augment component along a longitudinal axis of the at least one throughbore of the augment component.

* * * * *